United States Patent
Sarojini et al.

(10) Patent No.: US 6,743,264 B2
(45) Date of Patent: Jun. 1, 2004

(54) TWO STEP PERMANENT COLORING OF HAIR

(75) Inventors: Padmaja Sarojini, Saddle Brook, NJ (US); John Brian Bartolone, Bridgeport, CT (US); Alexander C. Chan, Cranbury, NJ (US)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 119 days.

(21) Appl. No.: 10/075,745

(22) Filed: Feb. 14, 2002

(65) Prior Publication Data

US 2003/0154562 A1 Aug. 21, 2003

(51) Int. Cl.$^7$ .................................................. A11K 7/13
(52) U.S. Cl. ...................... 8/405; 8/406; 8/408; 8/410; 8/411; 8/412; 8/421; 8/485
(58) Field of Search ............................ 8/405, 406, 408, 8/410, 411, 412, 421, 485

(56) References Cited

U.S. PATENT DOCUMENTS

| | | | |
|---|---|---|---|
| 2,934,396 A | 4/1960 | Charle et al. ................ 8/11 |
| 3,194,734 A | 7/1965 | Seemuller et al. ............ 167/88 |
| 4,104,021 A | 8/1978 | Lapidus et al. ............... 8/10.2 |
| 4,314,810 A | 2/1982 | Fourcadier et al. ........... 8/410 |
| 4,370,142 A | 1/1983 | Bugaut et al. ................ 8/407 |
| 4,804,385 A | 2/1989 | Grollier et al. ............... 8/423 |
| 4,888,027 A | 12/1989 | Grollier et al. ............... 8/423 |
| 5,173,085 A | 12/1992 | Brown et al. ................. 8/405 |
| 5,525,123 A | 6/1996 | Lorenz et al. ................ 8/408 |
| 5,580,357 A | * 12/1996 | Cotteret et al. ............... 8/408 |
| 5,804,171 A | 9/1998 | Audousset et al. ........... 724/70.1 |
| 5,876,465 A | 3/1999 | Terranova et al. ............ 8/409 |
| 6,527,814 B1 | 3/2003 | De La Mettrie et al. ...... 8/405 |

FOREIGN PATENT DOCUMENTS

| | | |
|---|---|---|
| EP | 0545257 B1 | 6/1993 |
| EP | 0722711 A1 | 7/1996 |
| EP | 0826669 A1 | 3/1998 |
| EP | 0827739 A1 | 3/1998 |
| GB | 823503 | 11/1959 |
| GB | 2205329 A | 12/1988 |
| WO | 01/28508 A1 | 4/2001 |

OTHER PUBLICATIONS

Copending application: Applicant: Patel et al., Ser. No.: 09/811,920, Filed: Mar. 19, 2001, Method and Composition for Gradual Permanent Coloring of Hair; UNUS No.: Y2–0530–HC, Case No.: J6691(C).
International Search Report Application No. PCT/EP 01400 mailed Aug. 26, 2003.

* cited by examiner

Primary Examiner—Yogendra N. Gupta
Assistant Examiner—Eisa Elhilo
(74) Attorney, Agent, or Firm—Michael P. Aronson

(57) ABSTRACT

A method for treating hair which comprises:
- first contacting said hair with a substantially inactive mixture of oxidative hair dye precursors; and
- allowing said mixture to remain in said hair for a period of about 30 seconds to about 60 minutes;
- followed by contacting said hair with a developer to achieve long lasting hair color change, is described.

21 Claims, No Drawings

TWO STEP PERMANENT COLORING OF HAIR

BACKGROUND OF THE INVENTION

The present invention relates to methods and compositions for the permanent coloring of hair which provides long lasting hair color. The present invention also relates to methods for the coloring of hair which does not require the pre-mixing of hair colorant compositions and developers just prior to application, and which can avoid the staining of hands and clothes which often occurs during conventional permanent hair coloring processes.

Permanent hair color conventionally comes in two parts: a dye solution and a developer solution. In a conventional permanent hair coloring treatment, the dye solution and the developer solution are mixed and then applied to the hair, which is then left for about 25 to about 45 minutes. The hair is then rinsed with water, treated with a post treatment conditioner, and then rinsed again with water.

The application of the dye solution and the developer solution affords permanent hair coloring. However, use of this conventional method does not provide maximum color deposition or retention. In fact, in the subsequent rinse steps, a significant amount of hair color can be washed out.

It would be desirable to develop methods and compositions for permanently coloring hair that maximize the amount of hair color deposited and that minimize the amount of hair coloring that is washed out in the subsequent rinse steps.

By the methods of the present invention, durable or permanent, desired hair color, with longer lasting hair color change is achieved. Also in certain, permanent hair color embodiments of the present invention, the consumer does not have to undertake any mixing step. Also the consumer may not have to use a package which mixes two discrete compositions as they are being dispensed.

Patents and patent applications related to the field of this invention are as follows:

U.S. Pat. No. 5,525,123, discloses a hair dyeing composition based on oxidation dyestuff precursors which dyes and brightens the hair containing, besides at least one developer and at least one coupling agent, at least one metal salt and at least one ammonium compound selected from the group ammonium chloride, ammonium sulfate, ammonium carbonate, ammonium bicarbonate, and ammonium carbamate, having a pH-value between 8 and 11, preferably from 9 to 10, after admixture with an oxidizing agent in the ready-to-use preparation.

Co-owned and co-pending serial No. 09/811,920 filed Mar. 19, 2001 discloses a method for permanently dyeing hair which comprises subjecting said hair to a number of treatments, having a set time interval between each two consecutive such treatments, wherein each treatment comprises steps a.) and b.) below:
  a.) contacting said hair, for a period of about 5 seconds to about 5 minutes with a recently made mixture of:
    i.) an alkaline composition comprising a dye intermediate in a shampoo base or in a conditioner base; and
    ii.) an acidic composition comprising an oxidating compound in a shampoo base or in a conditioner base;
  b.) rinsing said mixture from said hair with water;
  with the proviso that when a conditioner base is present in a.) i.) above, an independently selected conditioner base is also present in a.) ii.) above; and when a shampoo base is present in a.) i.) above, an independently selected shampoo base is also present in a.) ii.) above;
and wherein said number of treatments is between about 2 to about 30; and wherein said set time interval between each two consecutive treatments is between about 8 hours and 30 days, is described.

SUMMARY OF THE INVENTION

The invention relates to methods and compositions for achieving permanent hair color change wherein said methods comprise the following steps:
1) contacting said hair with a substantially inactive mixture of oxidative hair dye precursors (the hair colorant part) at a pH of about 8 or about 7 or below for a period of about 30 seconds to about 60 minutes; and
2) contacting said hair with an oxidizing compound (the hair color developer part) at a pH of about 8 to about 11 for a period of about 30 seconds to about 60 minutes; and
3) rinsing said hair with water.

DETAILED DESCRIPTION OF THE INVENTION

As used herein % means weight % unless otherwise indicated. When used herein % refers to weight % as compared to the total weight percent of the composition that is being discussed. For example, when % is used to discuss the amount of an ingredient that is in the hair colorant part, this means weight % as compared to the total weight of the hair colorant part. When weight % of the hair color developer part is mentioned, this means the weight % as compared to the total weight of the hair color developer part. When the ratio of the hair colorant part to the hair color developer part is discussed this means the ratio of weight % of the hair colorant part to weight % of the hair color developer part.

As used herein "inactive" or "substantially inactive" means that the oxidation hair dye precursors are not chemically reacting or are not chemically reacting to a substantial degree, so as to form coupled or polymerized hair color molecules, or it means that the oxidation hair dye precursors are not chemically reacting in a substantial manner so as to form coupled or polymerized hair color molecules.

"Hair colorant compositions of the invention" are used interchangeably with "hair coloring compositions" of the invention and "coloring compositions of the invention". "Hair colorant compositions of the invention" refers generally to those compositions of the present invention which comprise oxidative hair dye precursors. "Hair color developer compositions of the invention" are used interchangeably with "developer compositions" of the invention. "Hair color developer compositions of the invention" refers to those compositions of the invention which include a basifying compound that serves to activate the oxidizing agent that thereby causes the coupling, reacting or polymerization of the oxidative hair dye precursors.

As will be seen below, in some embodiments of the present invention, hair color developer compositions comprise for example just a basifying compound and water; and others comprise a mixture of a basifying compound and a peroxygen compound. As used herein the term "recently" means within a very short interval of time such as within a few seconds or minutes, such as within 0.01 seconds to 120 seconds, or within 0.1 seconds to 60 seconds, or within 0.5 second to within 30 seconds or within 2 seconds to within 20 seconds. Compositions of the invention may be made by means which are known in the art or which are analogous to those which are known in the art. Ingredients which are included in compositions of the invention are known in the art or may be made by means which are known in the art.

The present invention relates to methods and compositions for achieving the permanent coloring of hair which methods comprise 1) contacting the hair with a substantially inactive mixture of oxidation hair dye precursors for a period of about 30 seconds to about 60 minutes, and then
2) contacting the hair with an oxidizing oxidative compound which causes said oxidation hair dye precursors to, react, couple, and polymerize so as to form large hair color molecules within the hair shaft; and
3) rinsing said hair with water.

The first step of the above method provides hair oxidation dye precursors with time to diffuse into the hair shaft. The second step of the above method causes the formation of larger sized hair color molecules within the hair shaft. Because of their size, these larger sized hair color molecules have a very low tendency for diffusing out of the hair shaft.

The following are two nonlimiting embodiments of methods of the present invention:

1) first, the substantially inactive mixture oxidation hair dye precursors may be applied to the hair in admixture with water and other water miscible solvents at about a neutral pH and allowed to remain on the hair for about 5 minutes to about 60 minutes;
2) then a recently made mixture of an oxidizing compound such as hydrogen peroxide, and a basifying compound such as NH$_4$OH, which serves to activate the oxidizing compound, is applied to the hair for about 5 minutes to about 60 minutes;
3) this latter mixture of oxidizing compound and basifying compound causes oxidation hair dye precursors which have already diffused into the hair shaft in step 1) to react, couple, and polymerize so as to form larger hair coloring molecules which have a low tendency to diffuse out of the hair shaft—thus causing the formation of permanent hair color.

A second nonlimiting embodiment of a method of the invention is as follows:

1) first, a substantially inactive mixture of oxidative hair dye precursors and an oxidizing agent such as hydrogen peroxide at an acidic pH, may be applied to the hair and allowed to remain upon the hair for about 5 to about 60 minutes.

During this time, because said mixture is acidic, the oxidizing compound is not reactive, and the oxidation hair dye precursors do not react together, but instead diffuse into the hair shaft.

2) then a mixture of a basifying agent, such as NH$_4$OH is applied to the hair so as to cause the oxidizing compound to become reactive and so as to cause the oxidation hair dye precursors to react, couple, and polymerize so as to form large hair color molecules within the hair shaft. This causes a large deposition of permanent hair color which will not wash out.

When the first above described embodiment of methods of the invention is involved, (that is, where the basifying compound and the oxidizing compound are applied as a mixture), the compositions of the invention may be as follows:

The hair colorant compositions of the invention may comprise:
a) about 0.001% to about 7.0% of an oxidation hair dye precursor;
b) optionally about 0.001% to about 7.0% of a second oxidation hair dye precursor; and
c) an aqueous carrier.

The hair colorant compositions of the invention may preferably comprise:
a) about 0.01% to about 5.0% of an oxidation hair dye precursor;
b) optionally about 0.01% to about 5.0% of a second oxidation hair dye precursor; and
c) an aqueous carrier.

The hair color developer compositions of the invention may comprise
a) about 0.1 to about 2% or about 3% or about 5% of an oxidative compound;
b) about 0.1 to about 1.5% or about 2.0% of a basifying compound; and
c) an aqueous carrier.

The hair color developer compositions of the invention may preferably comprise
a) about 0.1 to about 1% of an oxidative compound;
b) about 0.1 to about 1% of a basifying agent; and
c) an aqueous carrier.

When the second above described embodiment of methods and compositions of the invention is involved, (that is, where the oxidation hair dyes are mixed in with the oxidizing compound at an acidic pH), the hair colorant compositions of the invention may be as follows:
a) about 0.001% to about 1.0% of an oxidation hair dye precursor;
b) optionally about 0.001% to about 1.0% of a second oxidation hair dye precursor;
c) about 0.1 to about 2% of an oxidizing compound; and
d) an aqueous carrier.

The hair colorant compositions of the invention may be preferably as follows:
a) about 0.1% to about 0.8% of an oxidation hair dye precursor;
b) optionally about 0.1% to about 0.8% of a second oxidation hair dye precursor;
c) about 0.1 to about 1.5% of an oxidizing compound; and
d) an aqueous carrier.

In the second embodiment described above, the hair developer compositions of the invention may be preferably as follows:
a) about 0.1 to about 1.5% of a basifying compound; and
b) an aqueous carrier.

In the second embodiment described above, the hair developer compositions of the invention may be preferably as follows:
a) about 0.1 to about 1.0% of a basifying compound; and
b) an aqueous carrier.

A third embodiment of the compositions and methods of the present invention would involve three steps. The first would be application of the substantially inactive mixture of oxidation hair precursors for a period of about 30 seconds to about 60 minutes. The second would be an application of an acidic mixture of an oxidizing compound such as hydrogen peroxide, and the third step would be an application of a basifying compound for a period of about 5 minutes to about 60 minutes followed by rinsing.

The compositions and methods of the present invention may be used to color different types of hair such as Asian hair and Caucasian hair.

It will be understood by those skilled in the art that concentrations of oxidative hair dye precursors which may be employed in the present invention can be varied depending on, for example, the hair type which is to be colored and on the coloring effect which is desired.

What follows is a description of the ingredients that can be included in the compositions of the present invention.

Oxidative Hair Dye Precursors

The hair colorant compositions of the present invention can include one or more oxidative hair coloring precursors, agents or dyes. Such oxidative hair coloring agents are used in combination with the oxidizing systems of the present invention to deliver permanent hair dye to the hair.

Permanent hair dye compositions as defined herein are compositions, which once applied to the hair, are substantially resistant to washout.

The dye forming intermediates used in oxidative dyes can be aromatic diamines, naphthols, aminophenols and their derivatives. These dye forming intermediates can be classified as; primary and secondary intermediates, couplers and modifiers. As used herein the term "precursor" means precursor, coupler, modifier, and intermediate and the like. Primary intermediates are chemical compounds, which by themselves will form a dye upon oxidation. The secondary intermediates, also known as color modifiers or couplers, are used with other intermediates for specific color effects or to stabilize the color.

The oxidation dye intermediates, which are suitable for, use in the compositions and processes herein include aromatic diamines, naphthols, polyhydric phenols, aminophenols and derivatives of these aromatic compounds (e.g., N-substituted derivatives of the amines, and ethers of the phenols).

Primary oxidation dye intermediates are generally colorless molecules prior to oxidation. The oxidation dye color is generated when the primary intermediate is 'activated' and subsequently joined with a secondary intermediate (coupling agent), which is also generally colorless, to form a colored, conjugated molecule. In general terms, oxidation hair dye precursors or intermediates include those monomeric materials which, on oxidation, form oligomers or polymers having extended conjugated systems of electrons in their molecular structure.

Because of the new electronic structure, the resultant oligomers and polymers exhibit a shift in their electronic spectra to the visible range and appear colored. For example, oxidation dye precursors capable of forming colored polymers include materials such as p-phenylenediamine, which has two functional groups, are capable of oxidative polymerization to yield higher molecular weight colored materials having extended conjugated electron systems.

Color modifiers (couplers), such as those detailed hereinafter, are preferably used in conjunction with the oxidation dye precursors herein and are thought to interpose themselves in the colored polymers during their formation and to cause shifts in the electronic absorption spectra thereof, thereby resulting in slight color changes. A representative list of oxidation dye precursors suitable for use herein is found in Sagarin, "Cosmetic Science and Technology", "Interscience, Special Edition, Volume 2, pages 308 to 310 which is herein incorporated by reference.

It is to be understood that the oxidizing aids of the present invention are suitable for use (in combination with a source of peroxide as detailed herein) with all manner of oxidation dye precursors and color modifiers and that the precursors detailed below are only by way of example and are not intended to limit the compositions and processes herein.

The typical aromatic diamines, polyhydric phenols, aminophenols, and derivatives thereof, described above as primary dye precursors can also have additional substituents on the aromatic ring, e.g. halogen, alkyl, alkyl substituted additional substituents on the amino nitrogen and on the phenolic oxygen, e.g. substituted and unsubstituted alkyl and aryl groups.

The hair coloring compositions of the present invention may, in addition to the essential oxidative hair-coloring agents, optionally include non-oxidative and other dye materials. Optional non-oxidative and other dyes suitable for use in the hair coloring compositions and processes according to the present invention include semi-permanent, temporary and other dyes. Non-oxidative dyes as defined herein include the so-called 'direct action dyes', metallic dyes, metal chelate dyes, fiber reactive dyes and other synthetic and natural Chemical and Physical Behaviour of Human Hair '3rd Edn. by Clarence Robbins (pp 250–259); 'The Chemistry and Manufacture of Cosmetics'. Volume IV. 2nd Edn. Maison G. De dyes. Various types of non-oxidative dyes are detailed in: 'Navarre at chapter 45 by G. S. Kass (pp 841–920); 'cosmetics: Science and Technology' 2nd Edn, Vol. 11 Balsam Sagarin, Chapter 23 by F. E. Wall (pp 279–343); 'The Science of Hair Care' edited by C. Zviak, Chapter 7 (pp 235–261) and 'Hair Dyes', J. C. Johnson, Noyes Data Corp., Park Ridge, U.S.A. (1973), (pp 3–91 and 113–139).

Specific hair dyes which may be included in the compositions of the invention include m-aminophenol; 3-methyl-p-aminophenol; 2,3-dimethyl-p-aminophenol; p-phenylene diamine, p-toluenediamine; 2-chloro-p-phenylenediamine; N-phenyl-p-phenylenediamine; N-2-methoxyethyl-p-phenylenediamine; N,N-bis-(hydroxyethyl)-p-phenylenediamine; 2-hydroxymethyl-p-phenylenediamine; 2-hydroxyethyl-p-phenylenediamine; 4,4'-diaminodiphenylamine; 2,6-dimethyl-p-phenylenediamine; 2-isopropyl-p-phenylenediamine; N-(2-hydroxypropyl)-p-phenylenediamine; 2-propyl-p-phenylenediamine; 1,3-p-N,N-bis-(2-hydroxyethyl)-aminoanilino-2-propanol; 2-methyl-4-dimethylaminoaniline; p-aminophenol; p-methylaminophenol; 3-methyl-p-aminophenol;2-hydroxymethyl-p-aminophenol; 2-methyl-p-aminophenol; 2-(2-hydroxyethylaminomethyl)-p-aminophenol; 2-methoxymethyl-p-aminophenol; and 5-aminosalicylic acid; catechol; pyrogallol; o-aminophenol; 2,4-diaminophenol; 2,4,5-trihydroxytoluene; 1,2,4-trihydroxybenzene; 2-ethylamino-p-cresol; 2,3-dihydroxynaphthalene; 5-methyl-o-aminophenol; 6-methyl-o-aminophenol; and 2-amino-5-acetaminophenol; 2-methyl-1-naphthol; 1-acetoxy-2-methylnaphthalene; 1,7-dihydroxynaphthalene; resorcinol; 4-chlororesorcinol; 1-naphthol; 1,5-dihydroxynaphthalene; 2,7-dihydroxynaphthalene; 2-methylresorcinol; 1-hydroxy-6-aminonaphthalene-3-sulfonic acid; thymol (2-isopropyl-5-methylphenol); 1,5-dihydroxy-1,2,3,4-tetrahydronaphthalene; 2-chlororesorcinol; 2,3-dihydroxy-1,4-naphthoquinone; and 1-naphthol-4-sulfonic acid; m-phenylenediamine; 2-(2,4-diaminophenoxy)ethanol; N,N-bis(hydroxyethyl)-m-phenylenediamine; 2,6-diaminotoluene; N,N-bis(hydroxyethyl)-2,4-diaminophenetole; bis(2,4- diaminophenoxy)-1,3-propane; 1-hydroxyethyl-2,4-diaminobenzene; 2-amino-4 hydroxy-ethylaminoanisole; aminoethoxy-2,4-diaminobenzene; 2,4- diaminophenoxyacetic acid; 4,6-bis(hydroxyethoxy)-m-phenylenediamine; 2,4-diamino-5-methylphenetole; 2,4-diamino-5-hydroxyethoxytoluene; 2,4-dimethoxy 1,3-diaminobenzene; and 2,6-bis(hydroxyethylamino) toluene; m-aminophenol; 2-hydroxy-4-carbamoylmethylaminotoluene; m-carbamoylmethylaminophenol; 6-hydroxybenzomorpholine; 2-hydroxy-4-aminotoluene; 2-hydroxy-4-hydroxyethylaminotoluene; 4,6-dichloro-m-aminophenol; 2-methyl-m-aminophenol; 2-chloro-6-methyl-m-aminophenol; 2-hydroxyethoxy-5-aminophenol; 2-chloro-5-trifluoroethylaminophenol; 4-chloro-6-methyl-m-aminophenol; N-cyclopentyl-3-aminophenol; N-hydroxyethyl-4-methoxy-2-methyl-m-aminophenol and 5-amino-4-methoxy-2-methylphenol; 2-dimethylamino-5-aminopyridine; -tetra-aminopyrimidine; 4,5-diamino-1-methylpyrazole; 4,5-diamino-1-hydroxyethyl pyrazole, 4,5-diamino-1-hydroxyethyl pyrazole, 1-phenyl-3-methyl-5-pyrazolone; 6-methoxy-8-aminoquinoline; 2,6-dihydroxy-4-methylpyridine; 5-hydroxy-1,4-benzodioxane; 3,4-methylenedioxyphenol; 4-hydroxyethylamino-1,2-methylenedioxybenzene; 2,6-dihydroxy-3,4-dimethylpyridine; 5-chloro-2,3-dihydroxypyridine; 3,5-diamino-2,6-dimethoxypyridine; 2-hydroxyethylamino-6-methoxy-3-aminopyridine; 3,4-methylenedioxyaniline; 2,6-bis-hydroxyethoxy-3,5-diaminopyridine; 3-amino-5-hydroxy-2,6-dimethoxypyridine; 5,6-dihydroxyindole; 7-hydroxyindole; 5-hydroxyindole; 4-hydroxyindole; 2-bromo-4,5-methylenedioxyphenol; 6-hydroxyindole; 3-amino-2-methylamino-6-methoxypyridine; 2-amino-3-hydroxypyridine; 2,6-diaminopyridine; 5-(3,5-diamino-2-pyridyloxy)-1,3-dihydroxypentane; 3-(3,5-diamino-2-pyridyloxy)-2-hydroxypropanol and 4-hydroxy-2,5,6-triaminopyrimidine, or combinations thereof.

Solvents

Water is the preferred principal solvent, carrier or diluent for the compositions according to the present invention. As such, the compositions according to the present invention may include one or more solvents as additional solvent, carrier or diluent materials. Generally, the solvent is selected to be miscible with water and innocuous to the skin. Solvents suitable for use herein include $C_1$–$C_{20}$ mono- or polyhydric alcohols and their ethers, glycerine, with monohydric and dihydric alcohols and their ethers are preferred. In these compounds, alcoholic residues containing 2 to 10 carbon atoms are preferred. Thus, a particularly preferred group includes ethanol, isopropanol, n-propanol, butanol, propylene glycol, ethylene glycol monoethyl ether, and mixtures thereof.

These solvents may be present in the hair colorant compositions of the present invention. These solvents may be present in the hair color developer compositions of the present invention.

Buffering Agents

The hair colorant compositions and the hair developer compositions of the present invention may have widely ranging pH's. When basifying agents are present in compositions of the invention, the pH can range from about 7.0 to about 11.0. Acidic pH ranges of about 2.0 to about 4.0 may be employed in those embodiments of the present invention wherein oxidation hair precursors are applied to the hair in admixture with oxidizing compounds such as hydrogen peroxide. This is done because such low pH's will stabilize the hydrogen peroxide present.

The hair color developer compositions of the invention may have a preferred pH in the range of from about 7.0 or 8.0 to about 11, more preferably from about 8.0 to about 10.0.

Buffering agents may be present in the hair colorant compositions of the present invention and in the hair color developer compositions of the invention in order to maintain a desired pH level. The hair colorant compositions and the hair color developer compositions of the present invention may also contain one or more hair swelling agents (HSAs) such as urea, to adjust the pH to the desired level.

Several different pH modifiers can be used to adjust the pH of hair colorant compositions of the present invention and to adjust the pH of the hair color developer compositions of the present invention. Nonlimiting examples of suitable buffering agents are ammonium hydroxide, urea, ethylamine, dipropylamine, triethylamine and alkanediamines such as 1,3-diaminopropane, anhydrous alkaline alkanolamines such as, mono or di- or tri-ethanolamine, preferably those which are completely substituted on the amine group such as dimethylaminoethanol, polyalkylene polyamines such as diethylenetriamine or a heterocyclic amine such as morpholine as well as the hydroxides of alkali metals, such as sodium and potassium hydroxide, hydroxides of alkali earth metals, such as magnesium and calcium hydroxide, basic amino acids such as L-arginine, lysine, oxylysine and histidine and alkanolamines such as dimethylaminoethanol and aminoalkylpropanediol and mixtures thereof. Also suitable for use herein are compounds that form $HCO_3^-$ by dissociation in water (hereinafter referred to as 'ion forming compounds'). Nonlimiting examples of suitable ion forming compounds are $Na_2CO_3$, $NaHCO_3$, $K_2CO_3$, $(NH_4)_2CO_3$, $NH_4HCO_3$, $CaCO_3$ and $Ca(HCO_3)_2$ and mixtures thereof.

As herein before described, certain alkaline buffering agents such as ammonium hydroxide and monoethylamine (MEA), urea and the like, can also act as hair swelling agents (HSA's).

Preferred for use as buffering agents for the hair colorant compositions and the hair color developer compositions according to the present invention, which are alkaline, is ammonium hydroxide and/or sodium hydroxide.

Oxidizing Compounds

The oxidizing compounds or agents useful in the methods and compositions of the present invention are generally inorganic peroxygen materials capable of yielding peroxide in an aqueous solution. Inorganic peroxygen oxidizing agents are well known in the art and include hydrogen peroxide, inorganic alkali metal peroxides such as sodium periodate, sodium perbromate and sodium peroxide, and inorganic perhydrate salt oxidizing compounds, such as the alkali metal salts of perborates, percarbonates, perphosphates, persilicates, persulphates and the like. These inorganic perhydrate salts may be incorporated as monohydrates, tetrahydrates etc. Also useful are melamine peroxide, sodium perborate, and sodium percarbonate. Mixtures of two or more of such inorganic peroxygen oxidizing agents can be used. For all of these compounds, the active material is active hydrogen peroxide. One skilled in the art would recognize how much active hydrogen peroxide is desired in the hair coloring compositions that are being formulated and therefore one skilled in the art would be able to calculate how much of a peroxygen compound, such as for example, melamine peroxide, to employ.

Basifying Compounds

Basifying compounds may be contained in one or both of the hair colorant compositions and the hair color developer compositions of the invention. Basifying compounds may include, for example, $NH_4OH$.

In hair coloring kits of the invention which contain the hair colorant compositions of the present invention and the hair color developer compositions of the present invention, a portion of peroxide oxidizing agent, may be present in either solid or liquid form, such as hydrogen peroxide, and an acid buffering agent solution as mentioned above may be required to stabilize the hydrogen peroxide. Since hydrogen peroxide is stable in the pH range from 2 to 4, it may be necessary to use a buffering agent having a pH within this range. Dilute acids are suitable as hydrogen peroxide buffering agents. Phosphoric acid is a preferred agent for buffering hydrogen peroxide solutions.

This pH adjustment can be also effected by using well known acidifying agents in the field of treating keratinous fibers, and in particular human hair, such as inorganic and organic acids such as hydrochloric acid, tartaric acid, citric acid, and carboxylic or sulphonic acids such as ascorbic acid, acetic acid, lactic acid, sulphuric acid, formic acid, ammonium sulphate and sodium dihydrogenphosphate/phosphoric acid, disodium hydrogen phosphate/phosphoric acid, potassium chloride/hydrochloric acid, potassium dihydrogen phthalate/hydrochloric acid, sodium citrate/hydrochloric acid, potassium dihydrogen citrate/hydrochloric acid, potassium dihydrogencitrate/citric acid, sodium citrate/citric acid, sodium tartarate/tartaric acid, sodium lactate/lactic acid, sodium acetate/acetic acid, disodium hydrogenphosphate/citric acid and sodium chloride/glycine/hydrochloric acid and mixtures thereof.

Thickeners

Thickeners may be optionally included in the oxidation hair colorant compositions and hair developer compositions of the invention, and specifically thickeners may be included in the hair colorant part and the hair color developer parts of the invention. Long chain fatty alcohols having from about 11 to about 18 carbon atoms in the long fatty chain can be thickener constituents of the compositions of this invention. These alcohols can be used alone, or in admixture with each other. When included in the compositions, the alcohol is preferably present at from about 0.5 to about 10 weight percent of the composition, and more preferably at from about 2 to about 5 weight percent.

Lauryl alcohol, oleyl alcohol, myristyl alcohol, stearyl alcohol, and the like, and mixtures thereof are contemplated herein as thickeners. In addition, mixtures of natural or synthetic fatty alcohols having fatty chain lengths of from about 11 to about 18 carbons are also useful. Several such mixtures are available commercially, and are exemplified by the material containing a mixture of synthetic alcohols with 12 to 15 carbons in the alkyl chain sold under the trademark NEODOL 25 by Shell Chemical Company, and the material containing a mixture of synthetic alcohols with chain lengths of 12 to 16 carbons sold under the trademark ALFOL 1216 Alcohol by Conoco Chemicals.

Thickening agents suitable for use in the compositions herein may also be selected from oleic acid, cetyl alcohol, oleyl alcohol, sodium chloride, cetearyl alcohol, stearyl alcohol, synthetic thickeners such as Carbopol, ACULYN, STRUCTURE, and Acrosyl and mixtures thereof. Preferred thickeners for use herein are Aculyn 22 (RTM), steareth-20 methacrylate copolymer; Aculyn 44 (RTM) polyurethane resin and Acusol 830 (RTM), acrylates copolymer that are available from Rohm and Haas, Philadelphia, Pa., USA. Additional thickening agents suitable for use herein include sodium alginate or gum arabic, or cellulose derivatives, such as methyl cellulose or the sodium salt of carboxymethylcellulose or acrylic polymers.

Fatty alcohols of the above discussed carbon chain lengths which are ethoxylated to contain an average of one or two moles of ethylene oxide per mole of fatty alcohol can be used in place of the fatty alcohols themselves. Examples of such useful ethoxylated fatty acids include ethylene glycol cetyl ether, polyoxyethylene (2) stearyl ether, and the like; the exemplary compounds having CTFA Dictionary names of Ceteth-1 and Steareth-2, respectively.

Other Optional Ingredients

The hair colorant compositions and hair developer compositions of the invention, of the present invention can comprise a wide range of optional ingredients. Examples of these functional classes include: anticaking agents, antioxidants, binders, biological additives, bulking agents, chelating agents, chemical additives, colorants, cosmetic astringents, cosmetic biocides, denaturants, drug astringents, emulsifiers, film formers, fragrance components, humectants, opacifying agents, plasticizers, preservatives, propellants, reducing agents, solvents, foam boosters, hydrotropes, solubilizing agents, suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include solubilizing agents, sequestrants, amino acids, hydrolysed proteins and the like.

Other optional ingredients include organic acids. A non-exclusive list of examples of organic acids which can be used as the proton donating agent is adipic acid, tartaric acid, citric acid, maleic acid, malic acid, succinic acid, glycolic acid, glutaric acid, benzoic acid, malonic acid, salicylic acid, gluconic acid, polyacrylic acid, their salts, and mixtures thereof. A non-exclusive list of examples of mineral acid for use herein is hydrochloric, phosphoric, sulfuric and mixtures thereof.

Application of Methods and Compositions of the Invention

The hair colorant part and the hair color developer part of the present invention are applied to hair separately. By this it is meant that after the hair colorant part is contacted with the hair, a period of about 30 seconds to about 60 minutes is allowed to elapse before the hair color developer part is contacted with the hair. This is in sharp contrast to conventional permanent hair coloring methods which require that the hair be contacted with a hair colorant composition and a hair color developer composition, simultaneously or nearly simultaneously. Without being bound by theory, it is believed that an advantage of the methods of the present invention is that smaller hair dye precursor molecules are given time to diffuse into the hair shaft. Then when the hair is contacted with the hair color developer part, the smaller hair dye precursor molecules that are within the hair shaft undergo coupling and polymerization reactions so as to form larger color molecules that are trapped within the hair shaft because of their size. Another advantage of the methods of the present invention as compared to conventional permanent hair coloring methods, is that conventional permanent hair coloring methods cause much of the coupling and polymerization of the hair dye precursors to occur outside of the interior of the hair shaft and are wasted. Large hair color molecules are formed, and because of their size, these large hair color molecules cannot diffuse into the hair shaft.

The above physical phenomena can be described by the following chemical equations:

When rate of oxidation of hair dye precursors/rate of diffusion of hair dye precursors $\geq 1$;
diffusion of hair color precursor is limited by the rapid formation of dye molecules outside the hair fiber.

When rate of oxidation/rate of diffusion <1, diffusion of hair color precursor is not limited by the rapid formation of dye molecules outside the hair fiber.

The equipment used to measure both the initial color and color change on substrates (hair/skin) dyed with the singly packaged low pH coloring compositions of the present invention is a Hunter Colorquest spectrophotometer. The value used to express the degree of color change on any particular substrate is delta E ($\Delta E$). Delta E, as defined herein, is represented by a factual sum of L, a, and b values such that:

$$\Delta E = \text{is difference of color with undyed hair: } \sqrt{(\Delta L^2 + \Delta a^2 + \Delta b^2)}$$

and L is a measure of lightness and darkness (color intensity), wherein L=100 is equivalent to white, and L=0 is equivalent to black. Further, 'a' is a measure of the red and green quotients (color hues) such that positive equates to red and negative equates to green, and 'b'. is a measure of the yellow and blue quotients (color hues) such that positive equates to yellow and negative equates to blue.

The following examples below, which were made, are shown as illustrations only and are not intended to limit the scope of the invention.

The examples just below show that the two step process of the present invention results in longer lasting hair color change that is more resistant to methanol extraction, for example. The compositions which are used just below were prepared for these laboratory tests and do not include ingredients such as for example fragrances which would ordinarily be employed in commercial compositions.

EXAMPLE 1

| PAP/PAOC Pre-treatment Experiment. Shampoo extraction | | | | |
|---|---|---|---|---|
| PAP = p-Aminophenol<br>PAOC = p-Amino-o-Cresol | | Stock Solutions:<br>PAP = 5 wt % in milli-Q-water<br><br>PAOC = 2 wt % in Isopropanol<br>Hydrogen Peroxide ($H_2O_2$) = 30 wt %<br>Ammonium Hydroxide<br>($NH_3$) = 30 wt % | | |
| One-Step<br>Conventional Coloring<br>pH 10-Ex 1A | | | | |
| | Ingredients | Levels wt % | pH | Coloring Time |
| 0.4 wt % PAP +<br>0.45 wt % PAOC +<br>3.0 wt % $H_2O_2$ +<br>2 wt % $NH_3$ + milli-Q-water = 10 ml total | PAP | 0.40% | | |
| | PAOC | 0.45% | | |
| | $H_2O_2$ | 3.00% | | |
| | $NH_3$ | 2.00% | | |
| | Isopropanol | 22.50% | | |
| | Milli-Q-Water | 71.65% | | |
| | Total | 100.00% | PH10 | 45 min total |
| Two-Step Coloring<br>Process—Sample2-Ex.1 B | | | | |
| | Ingredients | Levels wt % | pH | Coloring Time |
| Step 1: 0.4 wt % PAP +<br>0.45 wt % PAOC +<br>milli-Q-water = 5 ml total, 20 min. | Step1<br>PAP | 0.40% | | |
| | PAOC | 0.45% | | |
| | Isopropanol | 22.50% | | |
| | Milli-Q-Water | 26.65% | | |
| | Total for Step 1 | 50.00% | pH 7 | 20 min |
| Step 2: 3 wt % $H_2O_2$ +<br>2 wt % $NH_3$ + milli-Q-water = 5 ml total,<br>25 min | Step 2<br>$H_2O_2$ | 3.00% | | |
| | $NH_3$ | 2.00% | | |
| | Milli-Q-Water | 45.00% | | |
| | Total for Step 2 | 50.00% | pH 10 | 25 min |
| Methanol Extraction<br>20 ml MeOH heated to 45 C. in glass container. 1 g dyed hair tress stirred 45 C. MeOH solution for 15 min. | | | | |
| | | After Dye | After MeOH Ext | Delta LAB values |

-continued

PAP/PAOC Pre-treatment Experiment. Shampoo extraction

| Description of Samples | I.D. | L | A | B | L | A | B | L | A | B |
|---|---|---|---|---|---|---|---|---|---|---|
| PAP + PAOC + NH₃/H₂O₂ conventional pH10. Dyed 45 min (CONTROL) SYSTEM A | C1 | 45.57 | 27.42 | 32.14 | 50.53 | 23.94 | 32.14 | 4.96 | −3.48 | 0.00 |
| Step 1: PAP + PAOC pretreatment 20 min Step 2: NH₃ + H₂O₂ dyed 25 min SYSTEM B | S2-1 | 44.97 | 29.78 | 33.69 | 46.81 | 26.97 | 32.55 | 1.84 | −2.81 | −1.14 |
| Step 1: PAP + PAOC pretreatment with ½ amt NH3 20 min Step 2: NH₃ + H₂O₂ dyed 25 min SYSTEM C | S3-1 | 47.59 | 25.91 | 30.70 | 53 | 25.44 | 31.75 | 5.41 | −0.47 | 1.05 |
| Step 1: ½ amt PAP + PAOC pretreatment 20 min Step 2: ½ amt PAP/PAOC + NH₃/H₂O₂ dye 25 min PAP/PAOC Shampoo Extraction 25 ml 10% Suave Lavender Shampoo/0.5 g dyed hair. Agitated for 30 min. | S4-1 | 46.78 | 26.91 | 31.16 | 49.98 | 23.94 | 31.06 | 3.20 | −2.97 | −0.10 |

| | | After Dye | | | After Shampoo Ext | | | Delta LAB Values | | |
|---|---|---|---|---|---|---|---|---|---|---|
| Description of Samples | I.D. | L | A | B | L | A | B | L | A | B |
| PAP + PAOC + NH₃/H₂O₂ Conventional pH10. Dyed 45 min (CONTROL) SYSTEM A | C1 | 45.30 | 26.75 | 31.12 | 48.07 | 22.9 | 31.02 | 2.77 | −3.85 | −0.10 |
| Step 1: PAP + PAOC pretreatment 20 min Step 2: NH₃ + H₂O₂ dyed 25 min SYSTEM B | S2-1 | 44.96 | 29.28 | 33.21 | 46.74 | 24.27 | 32.08 | 1.78 | −5.01 | −1.13 |
| Step 1: PAP + PAOC pretreatment with ½ amt NH₃ 20 min Step 2: NH₃ + H₂O₂ dyed 25 min SYSTEM C | S3-1 | 46.03 | 25.81 | 30.69 | 48.44 | 22.34 | 30.16 | 2.41 | −3.47 | −0.53 |
| Step 1: ½ amt PAP + PAOC pretreatment 20 min Step 2: ½ amt PAP/PAOC + NH₃/H₂O₂ dye 25 min | S4-1 | 46.81 | 26.43 | 31.00 | 48.02 | 20.52 | 28.06 | 1.21 | −5.91 | −2.94 |

Color Change/Color Control:

Using L as a value of color intensity in hair, it can be clearly observed that all 3 of the 2-step color systems found in Example 1 had better color retention compared to the conventional pre-mixed system.

EXAMPLE 2

Two-Step Coloring Process. Pre/Post Treatments at Alkaline pH

| Ingredients | Levels, wt. % | pH | Coloring time |
|---|---|---|---|
| Step1 | | | |
| p-Aminophenol | 0.40 | | |
| 4-Amino-3-hydroxytoluene | 0.45 | | 20 min |
| Ammonia (28%) | 2.0 | 10 | |
| Isopropanol | 22.50 | | |
| Milli-Q-Water | 24.65 | | |
| Step1 Total | 50 | | |
| Step2 | | | |
| Hydrogen Peroxide (30%) | 3.00 | | |
| Ammonia (28%) | 2.00 | 10 | |
| Milli-Q-Water | 45.0 | | 25 min |
| Step2 Total | 50 | | |
| Final Total | 100 | | |

Results: Hunter Lab values before extraction (after coloring) and after Shampoo and Methanol extractions

| | L | a | b |
|---|---|---|---|
| Before Extraction | 41.47 | 26.18 | 29.48 |
| After Methanol Extraction | 45.77 | 26.18 | 32.21 |
| After Shampoo Extraction | 43.01 | 25.44 | 29.79 |

EXAMPLE 3

Two-Step Coloring Process.—Pre-Treatment at Neutral pH and Post-Treatment at Alkaline pH

| Ingredients | Levels, wt. % | pH | Coloring time |
|---|---|---|---|
| Step 1: | | | |
| p-Aminophenol | 0.20 | | |
| 4-Amino-3-hydroxytoluene | 0.23 | 7 | 20 min |
| Isopropanol | 22.50 | | |
| Milli-Q-Water | 27.07 | | |
| Step1 Total | 50 | | |
| Step 2: | | | |
| p-Aminophenol | 0.20 | | |
| 4-Amino-3-hydroxytoluene | 0.23 | 10.0 | 25 min |
| Hydrogen Peroxide (30%) | 3.00 | | |
| Ammonia (28%) | 2.00 | | |
| Milli-Q-Water | 44.57 | | |
| Step2 Total | 50 | | |
| Final Total | 100 | | |

Results: Hunter Lab values before extraction (after coloring) and after Shampoo and Methanol extractions

| | L | a | b |
|---|---|---|---|
| Before Extraction | 46.78 | 26.91 | 31.16 |
| After Methanol Extraction | 49.98 | 23.94 | 31.06 |
| After Shampoo Extraction | 48.02 | 20.52 | 28.06 |

ADDITIONAL EXAMPLES

EXAMPLE 4

| Composition For The First Step: | | |
|---|---|---|
| Ceteareth 23 | | 3 |
| Cocoamidopropyl betaine | | 2 |
| Cetyl alcohol | | 2.3 |
| Propylene glycol | | 2.5 |
| p-Amino-o-cresol | | 2.2 |
| Sodium hydroxide | | 1.0 |
| p-Phenylenediamine | | 1.0 |
| Steareth 3 | | 0.8 |
| EDTA | | 0.1 |
| p-Aminophenol | | 0.5 |
| Isoascrobic acid | | 0.1 |
| Sodium bisulfite | | 0.2 |
| Fragrance | | 0.02 |
| Acetic acid | q.s | pH 7.5 |
| Water | q.s. | 100 |
| Composition For The Second Step: | | |
| Hydrogen peroxide | | 3.0 |
| Cetyl alcohol | | 2.0 |
| Ceteareth 23 | | 0.5 |
| Phosphoric acid | | 1.0 |
| Ammonia (28%) | q.s. | pH 10 |
| Water | q.s. | 100 |

The above compositions may be made by methods which are known in the art.

A dual package which can be employed in the products and kits of the present invention is disclosed in U.S. Pat. No. 6,082,588 to Markey et al which is hereby incorporated by reference.

Kit Containing an Instruction Sheet

The invention also relates to a kit for carrying out the hair coloring method of the invention. The kit may comprise a hair color developer solution, a hair colorant part and a post treatment solution, each in a separate container or in a dual container, as described herein. The kit also contains written instructions that explain how the compositions of the invention are used.

The consumer can admix the components of the kit according to written instructions, to obtain the aqueous reaction mixture. After treatment for a desired time the mixture of hair developer and hair dye may be removed, preferably with water or a conventional shampoo or a conventional conditioning shampoo.

Alternatively, and with respect to an embodiment of the invention wherein hair dye precursors are in admixture with the oxidizing compound, there is no need for the consumer to undertake a pre-mixing step, just prior to application to hair. The consumer contacts his or her hair with an admixture of hair dye precursors and the oxidizing compound and waits for about 5 minutes to about 60 minutes to elapse.

Then the consumer contacts his or her hair with the hair color developer mixture which is the basifying composition, and allows about 5 minutes to about 6-0 minutes to elapse, and then the consumer rinses the hair.

Desired change in hair color by the method of the invention is described by the mathematical formula described above. Desired change in hair color can be achieved in a number of other ways. In the first instance, the consumer can initially compare his or her hair color with desired hair color or the hair color of a sample tress. Hair dyeing by the method of the invention can be repeated until his or her hair color matches the desired hair color.

Desired hair color can also be reached by comparing hair after each treatment until it matches hair tresses taken from the consumer during a prior treatment.

Desired hair color can also be reached by testing the hair after each treatment with instruments, which measure the color of the hair. When the measurements of hair color of the treated hair reach a desired level, the treatment hair reach a desired level, the treatment can be stopped.

Indeed, reaching the desired hair color can be achieved by the use of any matching or comparison method commonly employed in the art.

The invention being thus described, it will be obvious that the same may be varied in many ways. Such variations are not to be regarded as a departure from the spirit and scope of the invention and all such modifications are intended to be included within the scope of the following claims.

What is claimed is:

1. A method for treating hair which comprises:
   (a) contacting said hair with a substantially inactive mixture of oxidative hair dye precursors wherein the rate of oxidation of hair dye precursors/rate of diffusion of hair dye precursors <1;
   (b) allowing said mixture to remain in said hair for a period of about 30 seconds to about 60 minutes;
   (c) contacting said hair with a composition comprising an oxidizing compound, a basifying compound, or mixtures thereof;
   (d) allowing the composition in step (c) to remain on said hair for a period of about 30 seconds to about 60 minutes.

2. A method according to claim 1, wherein said mixture of oxidative hair dye precursors comprises an oxidizing compound and said mixture has about an acidic pH to about a neutral pH.

3. A method according to claim 1, wherein said mixture of oxidative hair dye precursors comprises a basifying compound.

4. A method according to claim 1, which further comprises:
   a) contacting said hair with a basifying composition; and
   b) allowing said basifying compound to remain in said hair for a period of about 30 seconds to about 60 minutes.

5. A method according to claim 1, wherein said mixture of oxidative dye precursors are selected from the group consisting of m-aminophenol; 3-methyl-p-aminophenol; 2,3-dimethyl-p-aminophenol; p-phenylene diamine; p-toluenediamine; p-phenylenediamine; 2-chloro-p-phenylenediamine; N-phenyl-p-phenylenediamine; N-2-methoxyethyl-p-phenylenediamine; N,N-bis-(hydroxyethyl)-p-phenylenediamine; 2-hydroxymethyl-p-phenylenediamine; 2-hydroxyethyl-p-phenylenediamine; 4,4'-diaminodiphenylamine; 2,6-dimethyl-p-phenylenediamine; 2-isopropyl-p-phenylenediamine; N-(2-hydroxypropyl)-p-phenylenediamine; 2-propyl-p-phenylenediamine; 1,3-N,N-bis-(2-hydroxyethyl)-N, N-bis (4-aminophenyl)-2-propanol; 2-methyl-4-dimethylaminoaniline; p-aminophenol; p-methylaminophenol; 3-methyl-p-aminophenol; 2-hydroxymethyl-p-aminophenol; 2-methyl-p-aminophenol; 2-(2-hydroxyethylaminomethyl)-p-aminophenol; 2-methoxymethyl-p-aminophenol; and 5-aminosalicylic acid; catechol; pyrogallol; o-aminophenol; 2,4-diaminophenol; 2-ethylamino-p-cresol; 2,3-dihydroxynaphthalene; 5-methyl-o-aminophenol; 6-methyl-o-aminophenol; and 2-amino-5-acetaminophenol; 2-methyl-1-naphthol; 1-acetoxy-2-methylnaphthalene; 1,7-dihydroxynaphthalene; resorcinol; 4-chlororesorcinol; 1-naphthol; 1,5-dihydroxynaphthalene; 2,7-dihydroxynaphthalene; 2-methylresorcinol; 1-hydroxy-6-aminonaphthalene-3-sulfonic acid; thymol (2-isopropyl-5-methylphenol); 1,5-dihydroxy-1,2,3,4-tetrahydronaphthalene; 2-chlororesorcinol; 2,3-dihydroxy-1,4-naphthoquinone; and 1-naphthol-4-sulfonic acid; m-phenylenediamine; 2-(2,4-diaminophenoxy)ethanol; N,N-bis(hydroxyethyl)-m-phenylenediamine; 2,6-diaminotoluene; N,N-bis(hydroxyethyl)-2,4-diaminophenetole; bis(2,4-diaminophenoxy)-1,3-propane; 1-hydroxyethyl-2,4-diaminobenzene; 2-amino-4-hydroxyethylaminoanisole; aminoethoxy-2,4-diaminobenzene; 2,4-diaminophenoxyacetic acid; 4,6-bis (hydroxyethoxy)-m-phenylenediamine; 2,4-diamino-5-methylphenetole; 2,4-diamino-5-hydroxyethoxytoluene; 2,4-dimethoxy 1,3-diaminobenzene; and 2,6-bis (hydroxyethylamino) toluene; m-aminophenol; 2-hydroxy-4-carbamoylmethylaminotoluene; m-carbamoylmethylaminophenol; 6-hydroxybenzomorpholine; 2-hydroxy-4-aminotoluene; 2-hydroxy-4-hydroxyethylaminotoluene; 4,6-dichloro-m-aminophenol; 2-methyl-m-aminophenol; 2-chloro-6-methyl-m-aminophenol; 2-hydroxyethoxy-5-aminophenol; 2-chloro-5-trifluoroethylaminophenol; 4-chloro-6-methyl-m-aminophenol; N-cyclopentyl-3-aminophenol; N-hydroxyethyl-4-methoxy-2-methyl-m-aminophenol and 5-amino-4-methoxy-2-methylphenol; 2-dimethylamino-5-aminopyridine; 2,4,5,6-tetra-aminopyrimidine; 4,5-diamino-1-methylpyrazole; 4,5-diamino-1-hydroxymethyl pyrazole, 4,5-diamino-1-hydroxyethylpyrazole; 1-phenyl-3-methyl-5-pyrazolone; 6-methoxy-8-aminoquinoline; 2,6-dihydroxy-4-methylpyridine; 5-hydroxy-1,4-benzodioxane; 3,4-methylenedioxyphenol; 4-hydroxyethylamino-1,2-methylenedioxybenzene; 2,6-dihydroxy-3,4-dimethylpyridine; 5-chloro-2,3-dihydroxypyridine; 3,5-diamino-2,6-dimethoxypyridine; 2-hydroxyethylamino-6-methoxy-3-aminopyridine; 3,4-methylenedioxyaniline; 2,6-bis-hydroxyethoxy-3,5-diaminopyridine; 3-amino-5-hydroxy-2,6-dimethoxypyridine; 2-bromo-4,5-methylenedioxyphenol; 3-amino-2-methylamino-6-methoxypyridine; 2-amino-3-hydroxypyridine; 2,6-diaminopyridine; 5-(3,5-diamino-2-pyridyloxy)-1,3-dihydroxypentane; 3-(3,5-diamino-2-pyridyloxy)-2-hydroxypropanol; 4-hydroxy-2,5,6-triaminopyrimidine, and mixtures thereof.

6. A method according to claim 1 wherein said oxidation hair dye precursor composition comprises:
   (a) about 0.001% to about 1.0% of an oxidation hair dye precursor;
   (b) about 0.001% to about 1.0% of a second oxidation hair dye precursor; and
   (c) an aqueous carrier.

7. A method according to claim 1 wherein said oxidation hair dye precursor composition comprises:
   a) about 0.02% to about 0.1% of an oxidation hair dye precursor;
   b) optionally about 0.02% to about 0.1% of a second oxidation hair dye precursor; and
   c) an aqueous carrier.

8. A method according to claim 3 wherein said oxidation hair dye precursor composition comprises:
   a) about 0.01 to about 10% of an oxidative compound;
   b) about 0.01 to about 5% of a basifying compound; and
   c) an aqueous carrier.

9. A method according to claim 1 wherein said oxidative composition comprises
   a) about 0.1 to about 5.0% of an oxidative compound;
   b) about 0.1 to about 3.0% of a basifying agent; and
   c) an aqueous carrier.

10. A method according to claim 2 wherein said mixture of oxidative hair dye precursors comprises:
    a) about 0.001% to about 5.0% of an oxidation hair dye precursor;
    b) about 0.001% to about 3.0% of a second oxidation hair dye precursor;
    c) about 0.1 to about 4.5% of an oxidative compound; and
    d) an aqueous carrier.

11. A method according to claim 10 wherein said mixture of oxidative hair dye precursors comprises
    a) about 0.1% to about 3.0% of an oxidation hair dye precursors;
    b) about 0.1% to about 3.0% of a second oxidation hair dye precursor;
    c) about 0.1 to about 4.0% of an oxidative compound; and
    d) an aqueous carrier.

12. A method according to claim 1, wherein said mixture of oxidative hair dye precursors comprises:
    a) about 0.1 to about 1% of an oxidative compound;
    b) about 0.1 to about 3.0% of a second oxidation hair dye precursor;
    c) about 0.1 to about 1.5% of a basifying compound; and
    d) an aqueous carrier.

13. A method according to claim 1 wherein said oxidative compound is selected from the group consisting of hydrogen peroxide, urea peroxide, melamine peroxide, sodium perborate and sodium percarbonate.

14. A method according to claim 1, for treating hair which comprises providing said hair longer lasting color.

15. A kit for permanently coloring hair which comprises:
    a) a hair colorant composition comprising oxidative dye precursors in a container,
    b) a hair color developer composition in a container, and
    c) written instructions that direct that the hair colorant part is applied to the hair as a substantially inactive mixture for about 30 seconds to about 60 minutes before the hair color developer is applied to the hair,
    wherein the hair dye precursors of the hair colorant composition satisfies the condition that the rate of oxidation of hair dye precursors/rate of diffusion of hair dye precursors <1 when hair colorant composition is applied to the hair before the hair is contacted with the hair color developer composition.

16. A method according to claim 1 wherein the oxidative dye precursors comprises at least one primary intermediate and at least one coupler.

17. A method according to claim 1 wherein the oxidative dye precursors are selected from the group consisting of: p-phenylenediamine; p-aminophenol; p-amino-o-cresol; 4-amino-3-hydroxytoluene; and mixtures thereof.

18. A method according to claim 1 wherein the mixture of oxidative hair dye is allowed to remain on the hair in step b) for a period of from about 5 minutes to about 60 minutes.

19. A kit according to claim 15 wherein the oxidative dye precursors are selected from the group consisting of: p-phenylenediamine; p-aminophenol; p-amino-o-cresol; 4-amino-3-hydroxytoluene; and mixtures thereof.

20. A method according to claim 1 wherein the mixture of oxidative hair dye precursors is allowed to remain on the hair in step b) for a period of from about 20 minutes to about 60 minutes.

21. A kit according to claim 15 wherein the written instructions direct that the hair colorant part is applied to the hair as a substantially inactive mixture for about 5 minutes to about 60 minutes before the hair color developer is applied to the hair.

* * * * *